US009585694B2

(12) United States Patent
Rosenberg (10) Patent No.: US 9,585,694 B2
(45) Date of Patent: *Mar. 7, 2017

(54) METHOD AND APPARATUS FOR ARTIFICIAL INSEMINATION

(71) Applicant: Doron Rosenberg, Toronto (CA)

(72) Inventor: Doron Rosenberg, Toronto (CA)

(*) Notice: Subject to any disclaimer, the term of this patent is extended or adjusted under 35 U.S.C. 154(b) by 104 days.

This patent is subject to a terminal disclaimer.

(21) Appl. No.: 14/800,268

(22) Filed: Jul. 15, 2015

(65) Prior Publication Data

US 2015/0313638 A1 Nov. 5, 2015

Related U.S. Application Data

(63) Continuation-in-part of application No. 14/052,134, filed on Oct. 11, 2013, now Pat. No. 9,220,656.

(60) Provisional application No. 61/714,755, filed on Oct. 17, 2012.

(51) Int. Cl.
| *A61B 17/43* | (2006.01) |
| *A61H 23/02* | (2006.01) |
| *A61H 19/00* | (2006.01) |
| A61H 35/00 | (2006.01) |
| A61B 17/00 | (2006.01) |

(52) U.S. Cl.
CPC ............ *A61B 17/43* (2013.01); *A61H 19/44* (2013.01); *A61H 19/50* (2013.01); *A61H 23/02* (2013.01); *A61B 2017/00398* (2013.01); *A61B 2017/00734* (2013.01); *A61B 2560/0214* (2013.01); *A61H 23/0254* (2013.01); *A61H 35/00* (2013.01); *A61H 2201/0153* (2013.01); *A61H 2201/10* (2013.01); *A61H 2201/50* (2013.01)

(58) Field of Classification Search
CPC ...... A61H 19/00; A61H 19/02; A61H 19/027; A61H 19/44; A61H 2201/105; A61H 2201/1253; A61B 17/425; A61B 17/43
USPC .......................................... 600/38–41, 33–35
See application file for complete search history.

(56) References Cited

U.S. PATENT DOCUMENTS

| 3,910,275 | A | 10/1975 | Babey | |
| 9,220,656 | B2* | 12/2015 | Rosenberg | A61H 19/44 |
| 2008/0065187 | A1 | 3/2008 | Squicciarini | |
| 2011/0224482 | A1 | 9/2011 | McCarthy et al. | |
| 2012/0310040 | A1 | 12/2012 | Bollinger | |
| 2013/0324792 | A1* | 12/2013 | Mizrahi | A61H 19/44 |
| | | | | 600/38 |
| 2014/0200400 | A1* | 7/2014 | Berman | A61B 17/43 |
| | | | | 600/38 |

* cited by examiner

*Primary Examiner* — John Lacyk
(74) *Attorney, Agent, or Firm* — Nasser Ashgriz; UIPatent Inc.

(57) ABSTRACT

The object of the invention is to provide a device and means for artificial insemination. The present invention provides two methods of sperm delivery that aim to increase the success of intracervical artificial insemination. The shape and design of the present invention also allows artificial insemination to be a pleasurable experience.

10 Claims, 12 Drawing Sheets

METHOD AND APPARATUS FOR ARTIFICIAL INSEMINATION

RELATED APPLICATIONS

This application is a continuation of U.S. patent application Ser. No. 14/052,134 filed Oct. 11, 2013 which claims priority to U.S. Provisional Patent Application Ser. No. 61/714,755, filed Oct. 17, 2012, the contents of all of which are incorporated herein by reference.

FIELD OF THE INVENTION

The present invention relates to apparatus and method for artificial insemination and more specifically to an apparatus and method that functions for both fertilization and pleasure.

BACKGROUND OF THE INVENTION

The present invention is a method for sexual partners or individuals wishing to artificially inseminate. Artificial insemination (AI) can be performed in a clinic or at home using a variety of techniques. Intracervical insemination (ICI) is the method for the deposition of fresh or frozen sperm into the cervix. Generally, in order to achieve the best success with each treatment the AI and ICI procedures are performed at a medical clinic and by medical professionals. Undergoing such procedures can lead to stress in both partners and may result in an unpleasant experience for some.

The advantages of using an ICI device as opposed to other methods of AI are that it does not require sperm "washing" (the separation of sperm from the seminal fluid); it is a relatively fast procedure, and it is painless. Other methods of fertilization, such as intrauterine insemination, in vitro fertilization, and surrogacy are much more costly and/or are to be performed by physicians. ICI may be performed at home with the aid of a partner or alone as long as there is a sperm donor. ICI is also not as expensive as the above physician-performed methods.

The success of a single type of fertility treatment, whether ICI or otherwise, may be dependent on a number of factors. Two factors that have not been addressed in the prior art are ensuring the accurate delivery of a large amount of sperm cells to the correct location on the cervix, and the ability of female orgasm or female sexual pleasure to increase the sperm uptake into the uterus and thus increase the probability of fertilization.

ICI systems and methods are widespread and are characterized by their accessibility and lower difficulty level. Previous patents such as the U.S. Pat. No. 6,511,415 and U.S. Pat. No. 8,323,178 have focused solely on the delivery of the sperm in the vaginal canal without considering the potential pleasurable aspects of the act. Of course, the feeling of intimacy may be lost when attempting the procedure at a clinic or using devices, which resemble surgical devices. It may be preferable to use a device that provides a more pleasurable feeling during the procedure.

U.S. application Ser. No. 12/721,094 discloses a sexual device that will allow a wearer to artificially inseminate a partner, as well as being used to provide sexual pleasure. However, sperm delivery is accomplished manually using a syringe. This method of delivery may most likely lead to incorrect delivery if applied by laypersons not trained in AI. During ICI, sperm must be delivered into the cervix with a precise velocity so that the sperms can reach the surface of the cervix during expulsion. If the delivery velocity is too small, sperms may not reach the cervix and if it is too large sperms may be reflected off the walls of the cervix. The volume of sperm delivered is also important in the success of AI process. If the volume delivered is too small, there may be an back flow out of the cervical canal which may result in insufficient insemination. In order to increase the success of fertility it is most important to properly control the flow of sperm toward the cervical canal.

Devices and methods that are used in ICI require a physician to visually identify the cervix by the use of a speculum and then begin the release of sperm from the device. For best results, the contact with the cervix has to be observed visually during the procedure. Personal or home ICI kits such as described in the U.S. application Ser. No. 12/721,094 do not disclose methods for ensuring the delivery of sperm to the cervix and only provide methods and devices for depositing it in the vaginal canal. For these reasons, it is difficult for an at home ICI device to be as successful as ICI treatments performed at a clinic by medically trained professionals.

The present invention is designed to provide a greater success in AI. It is comprised of a means for ejecting the sperm at a specific velocity so that it ensures the best delivery to the cervix. The present invention also provides sexual pleasure. By incorporating an sperm injection system into a sex toy, the likelihood of the fertilization substantially increases.

SUMMARY OF THE INVENTION

The present invention aims to provide an effective solution for couples with fertility problems, same-sex couples or other persons such as choice mothers wishing to conceive a baby by ICI while also deriving sexual pleasure in the process. Additionally, the current invention also aims to increase the success of current conventional home based ICI methods.

The first objective of the present invention is to provide a device and method for the delivery of sperm to the cervix. As such, the present invention is comprised of an inner tube that allows sperm to be expelled from a capsule somewhere in the body of the device to an opening at the distal end and out of the device. The syringe stores sperm or any other type of liquid until the time the user determines when it is ready to be expelled. The sperm or liquid container may also be a conception cap or another type of capsule that is able to store the sperm.

The second objective of the present invention is to provide a more reliable method of sperm entry into the cervical canal and consequently to the uterus. The present invention comprises of a syringe pump mechanism to deliver a steady jet of sperm to the cervix. This method of delivery ensures that most of the sperm arrive at the intended target.

The third objective of the invention is to provide a sperm delivery method that is pleasurable to the recipient. For this purpose, the present invention is shaped like a dildo. A dildo is a sexual device that structurally may resemble a penis, and is a device that can be used by people of all genders and sexual orientation. Insertion of the device may resemble sexual intercourse and may result in pleasurable sensations for the recipient. The present invention is also capable of being attached to a harness as well as providing other ways of attachment during its use.

An additional feature of the invention that can be used to provide pleasure is its vibrating function. The female orgasm has been shown to result in increased ability of the uterus to uptake sperm deposited in the vagina, thus increasing the probability of fertility.

The objects features and effects of the invention are described in details below with accompanied drawings and embodiments.

The aforementioned objects of the present invention are attained by an apparatus and method that functions for fertilization. Other objects, advantages and novel features of the present invention will become readily apparent from the following drawings and detailed description of preferred embodiments.

BRIEF DESCRIPTION OF THE DRAWINGS

Embodiments herein will hereinafter be described in conjunction with the appended photos provided to illustrate and not to limit the scope of the claims, wherein like designations denote like elements, and in which:

FIG. 1 (*a-c*) show the perspective views of the apparatus;

FIG. 2 (*a-c*) show the perspective views of the apparatus;

FIG. 3 (*a-c*) show the perspective views of the apparatus without the sheaths;

FIG. 4 (*a-b*) show the perspective views of the apparatus with locking mechanism;

FIG. 5 (*a-b*) show the perspective views of the apparatus with locking mechanism and a sperm container with a plunger;

FIG. 8 (*a-b*) show the perspective views of the apparatus with a sperm container, a plunger and mechanical and electrical components of the base;

FIG. 9 (*a-b*) show the cross sectional views of the apparatus with a sperm container with a plunger and an ejecting mechanism;

DETAILED DESCRIPTION OF THE PREFERRED EMBODIMENTS

The present invention and the various features and advantages details thereof are explained more fully with reference to the non-limiting embodiments described in detail in the following description.

The present invention is directed to a mechanized apparatus that is particularly effective in stimulating female genitalia and has an ability to deliver sperm to the cervix in at a proper time.

Figure 1:
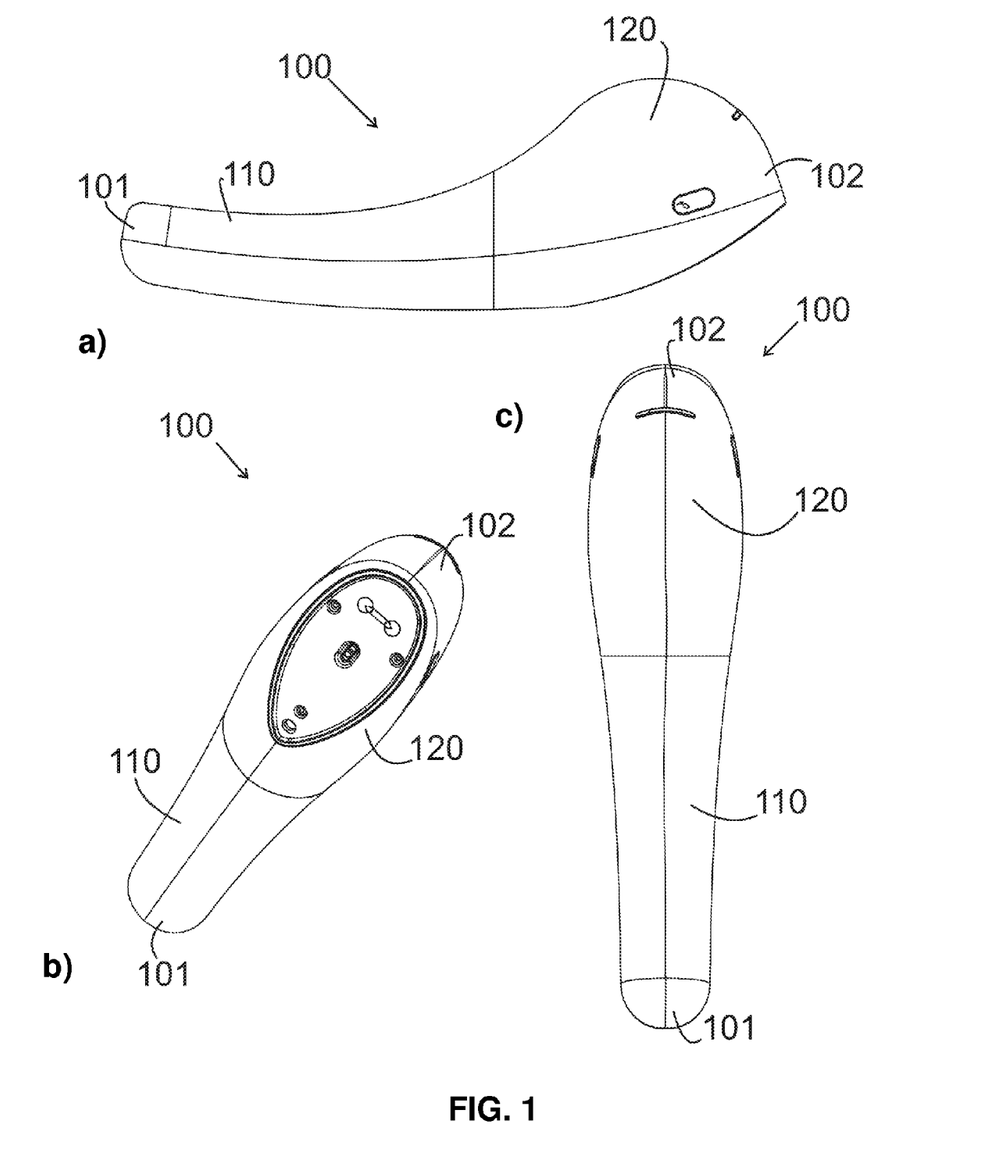

FIGS. 1 (*a-c*) and 2 (*a-c*) show the perspective views of an apparatus 100 for artificial insemination. The apparatus 100 comprises of two main parts that are located on a distal end 101 and a proximal end 102 of the apparatus 100. These two parts 110 and 120 are detachable for maintenance and other purposes.

The apparatus 100 comprises of a cylindrical body 110 resembling a dildo and a base 120 that embedded the components of the present invention. The present invention comprises of an exterior cover and an interior housing. The exterior cover acts as a sheath to be surrounding around the interior housing of the present invention. The sheath can be made of vinyl, latex and silicone. Silicone in particular is contact with the user's body and allowed a greater degree of realism.

Figure 2:
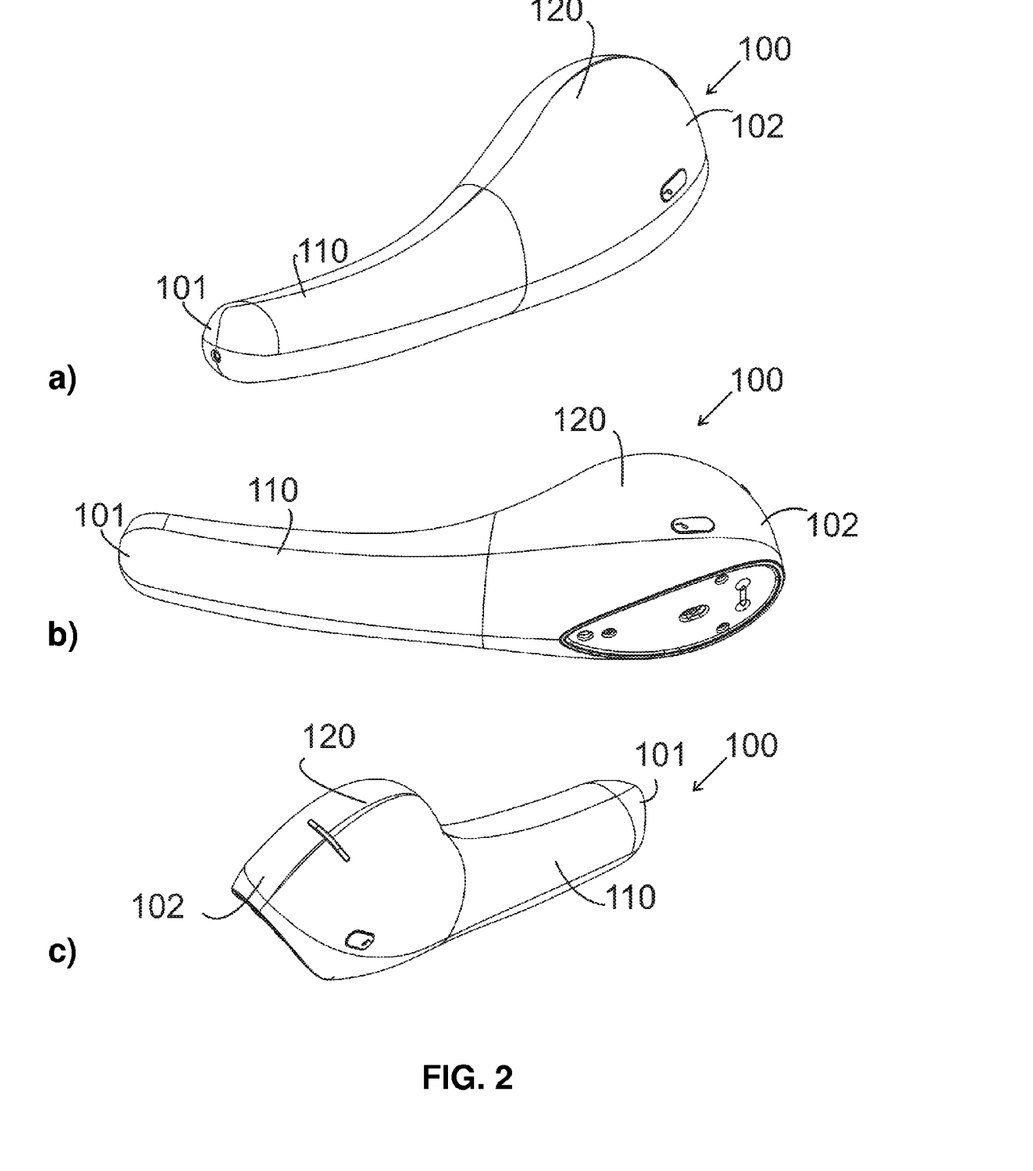
Figure 3:
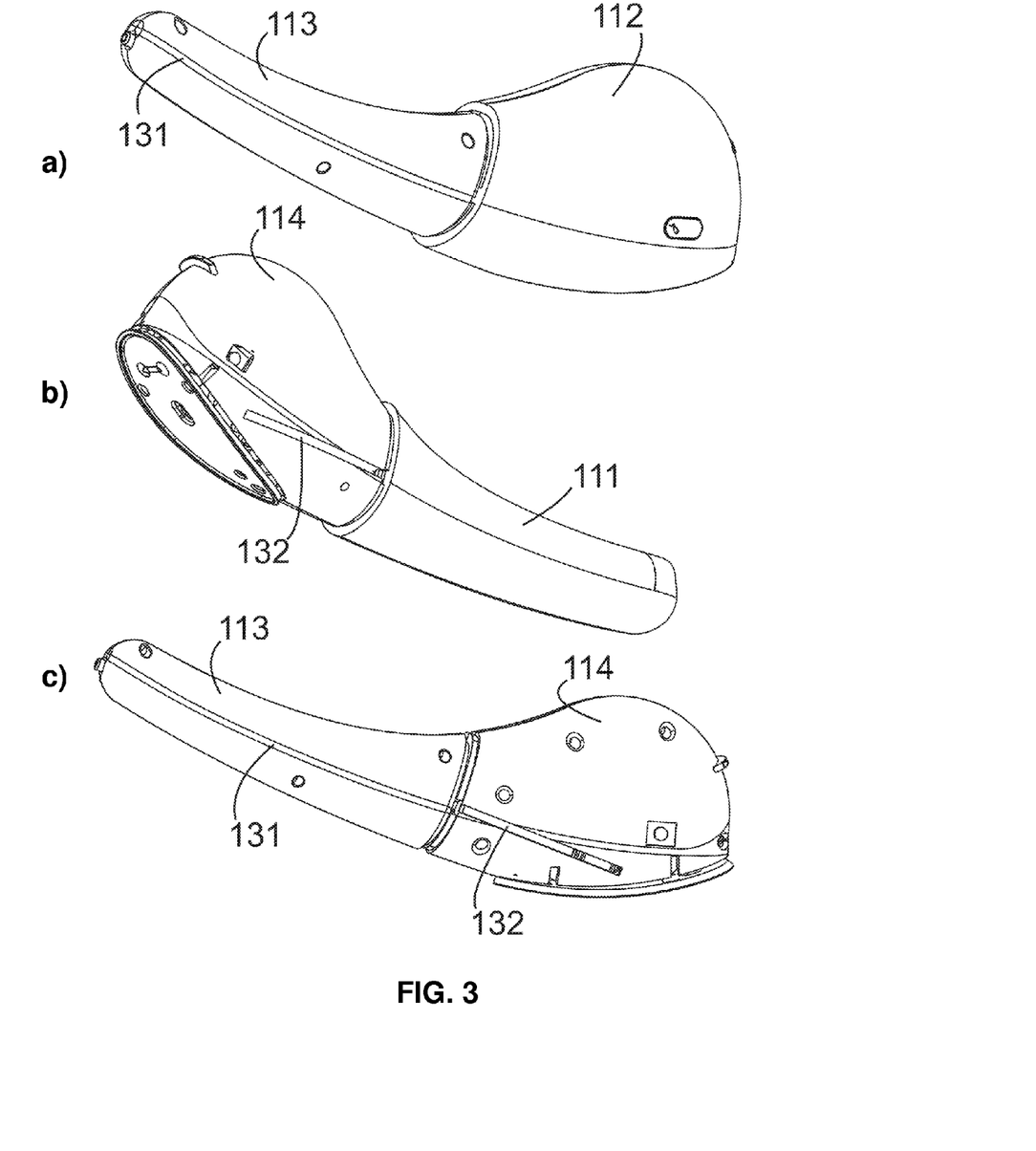

As shown in FIGS. 1-3, the present invention has two sets of sheaths 111-112. The first sheath 111 covers a cylindrical housing 113 of the apparatus 100. The cylindrical housing 113 and the first sheath 111 resemble phallic symbol for the apparatus 100 to stimulate the female genitalia. The second sheath 112 covers a base housing 114, the base housing 114 embedded the electrical and mechanical components of the present invention.

As shown in FIG. 3, the first sheath 111 can be removed by sliding it out of the cylindrical housing 113. A tongue and groove joint is used to secure the first sheath 111 on the cylindrical housing 113. There are two symmetrical grooves 131 designed in the interior body of the cylindrical housing 113.

Again as shown in FIG. 3, the second sheath 112 can be removed by sliding it out of the base housing 114. The same mechanism of groove and tongue is used to secure the second sheath 112 on the base housing 114. There are two symmetrical grooves 132 designed in the interior body of the base housing 114.

In the normal usage of the present invention, there is no need to remove the first and the second sheaths 111-112 from the housings 113-114. The user can put the sperm capsule inside the apparatus 100 or replace the battery without removing the sheaths 111-112.

Figure 4:
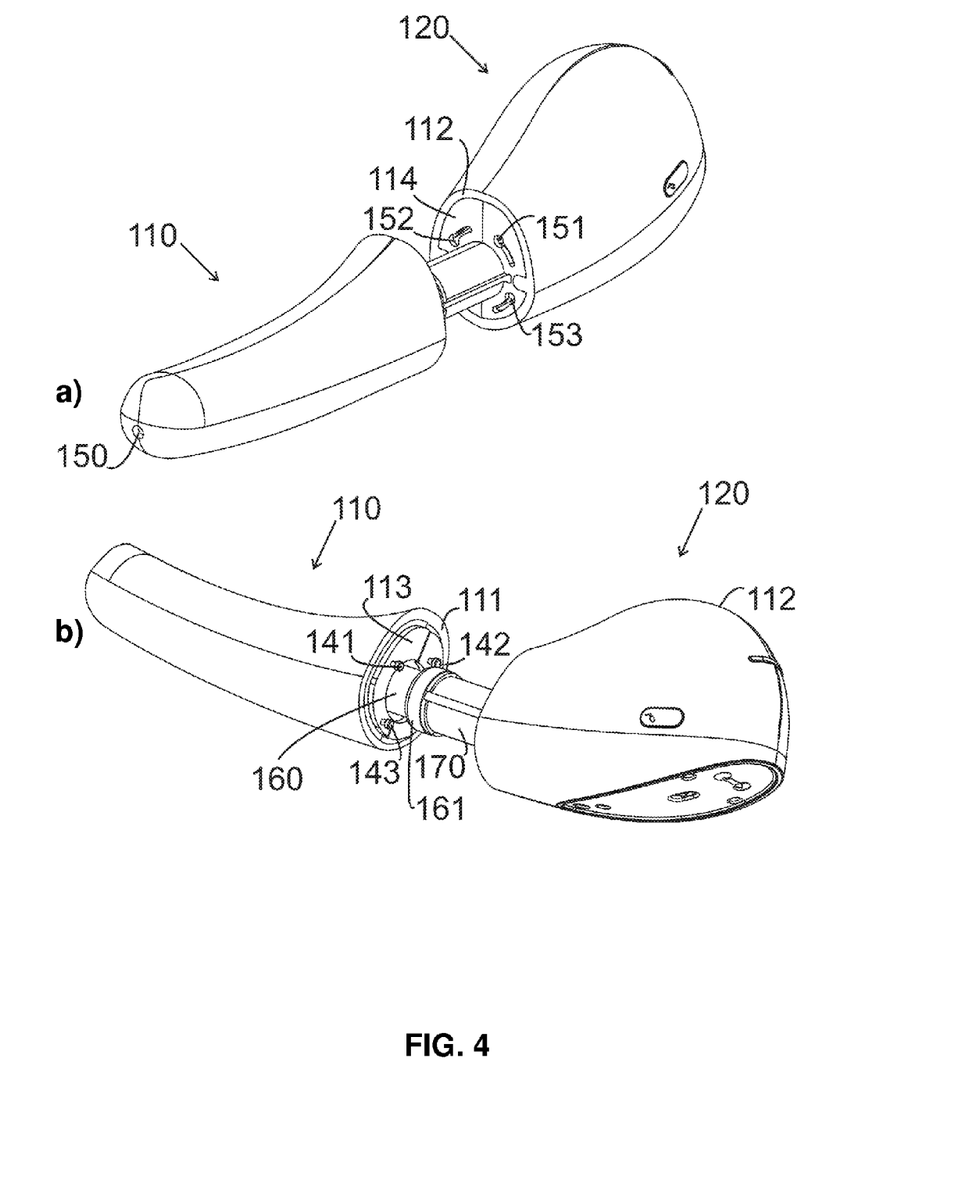

FIG. 4 illustrates the locking mechanism of the cylindrical body 110 on the base 120. Two pairs of pins 141-144 are extend axially from the distal end of the cylindrical body 110 to receive two sets of horn-shaped holes 151-154. Pins 141-144 have a round top sized to receive a top part of the horn-shaped holes 151-154. The cylindrical body 110 is secured on the base 120 by turning it clockwise when the pins enter the holes 151-154.

Figure 5:
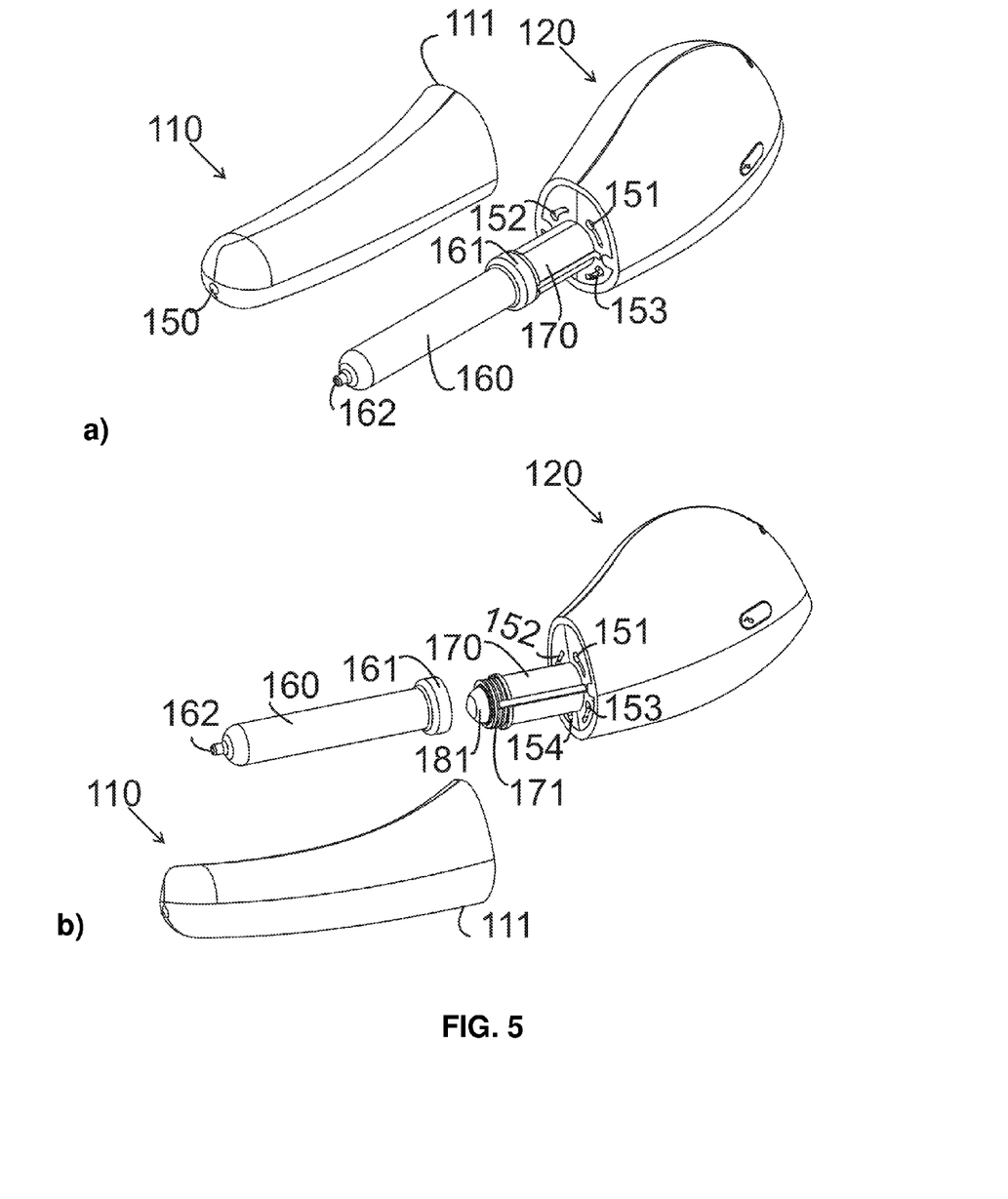

As shown in FIG. 5, the user can open the cylindrical body 110 and put the sperm capsule or any liquid inside a sperm container 160. The sperm container 160 is threaded such that it is engaged by a thread 171 of a syringe housing holder 170. As shown in FIG. 5 (*b*), a plunger 181 directs the liquid to the proximal end 162 of the sperm container 160.

Figure 6:
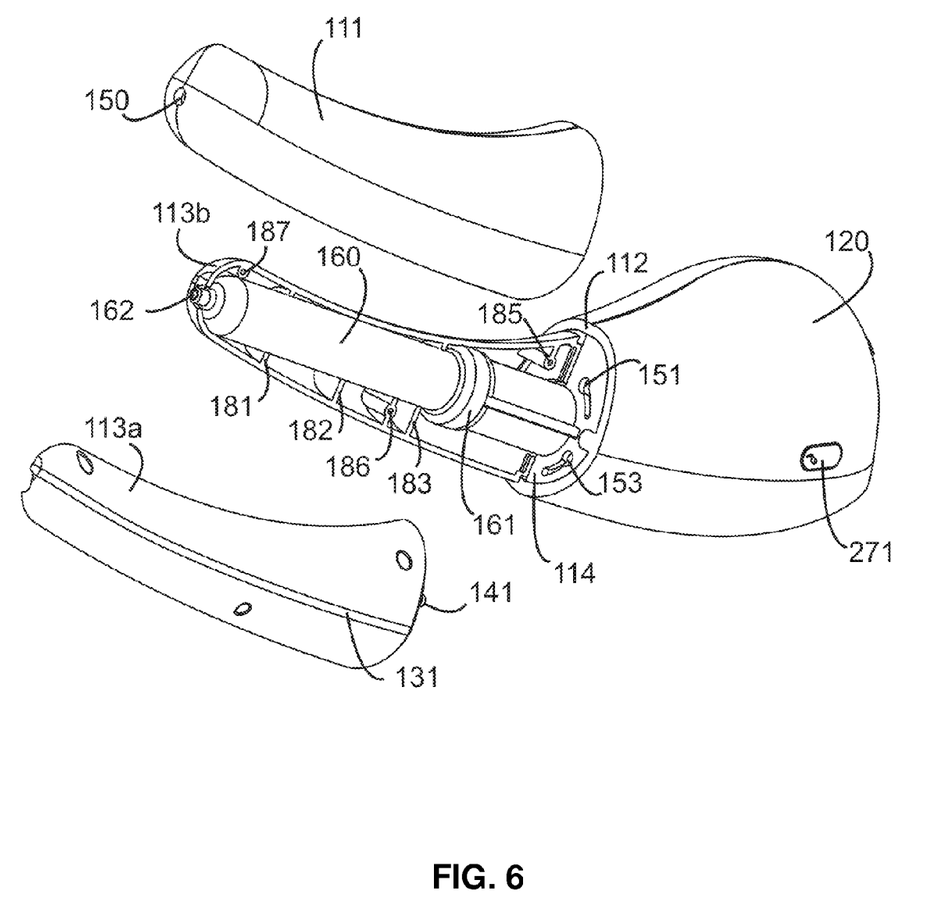
FIG. 6 shows the perspective views of the apparatus with locking mechanism and a sperm container with a plunger and a cylindrical housing.
Figure 7:
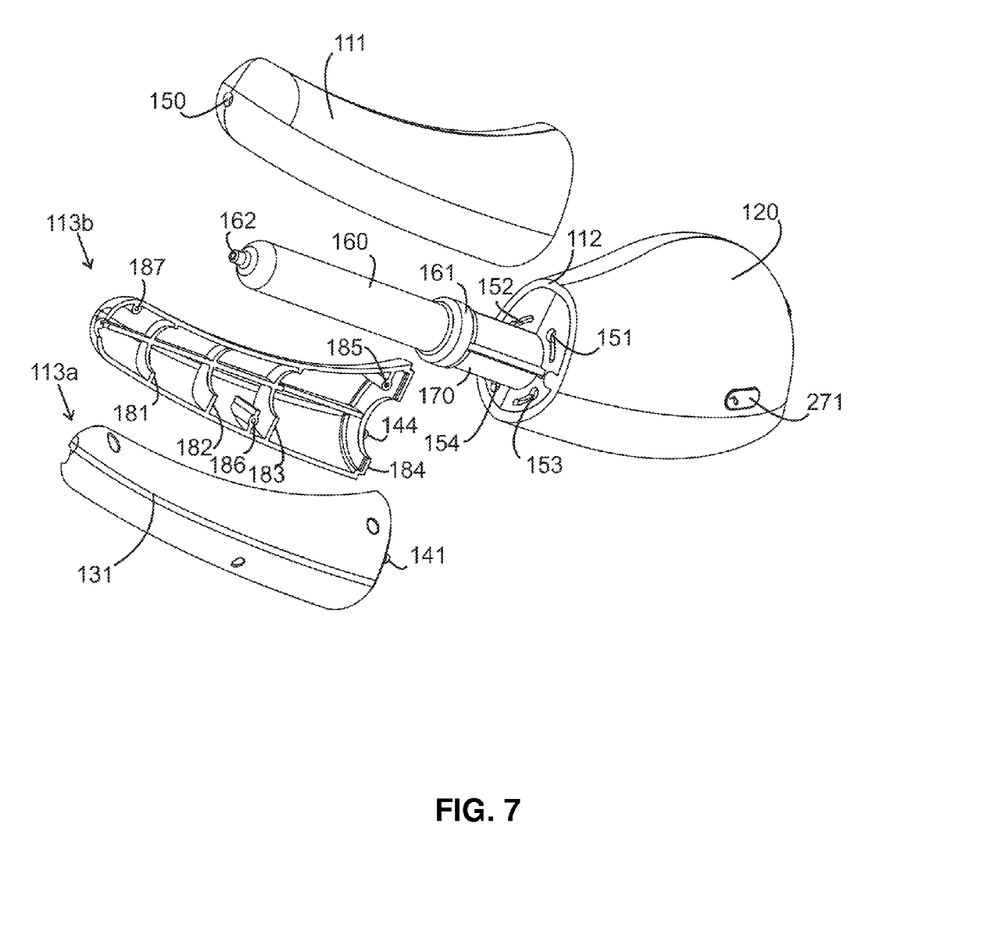
FIG. 7 shows the perspective views of the apparatus with locking mechanism and a sperm container with a plunger and cylindrical housings.

As shown in FIGS. 6-7, the cylindrical housing 113 has two symmetrical parts 113 (*a-b*). There is a plurality of supporting edges 181-184 designed in the interior portion of the cylindrical housing 113 to keep the sperm container 160 in a proper place. For delivering the sperm by the syringe, the sperm container 160 should be in a proper position and being tight in all time. The supporting edges 181-184 have a curved surface to keep the sperm container 160 tight in a place.

Again as shown in FIGS. 6-7, two symmetrical parts 113 (*a-b*) of the cylindrical housing 113 are connected by three screws (not shown) and three nuts 185-187 to each other's.

Figure 8:
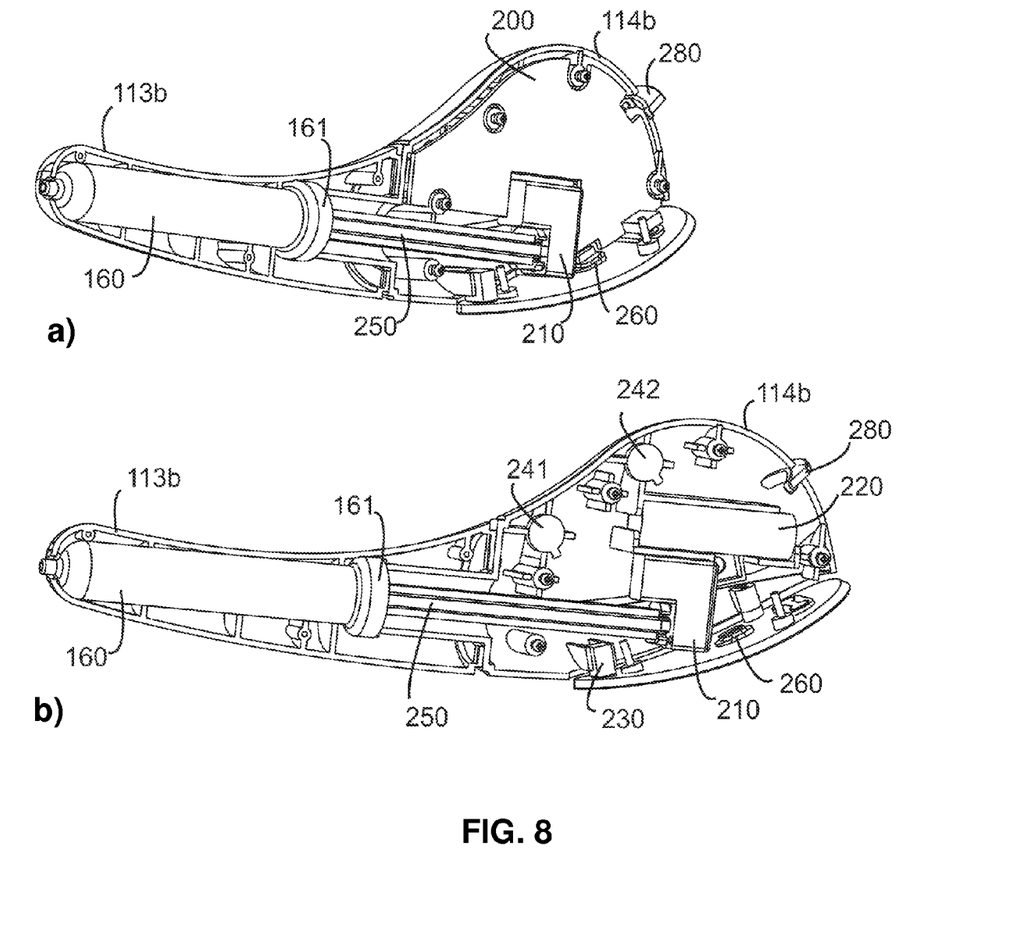
Figure 9:
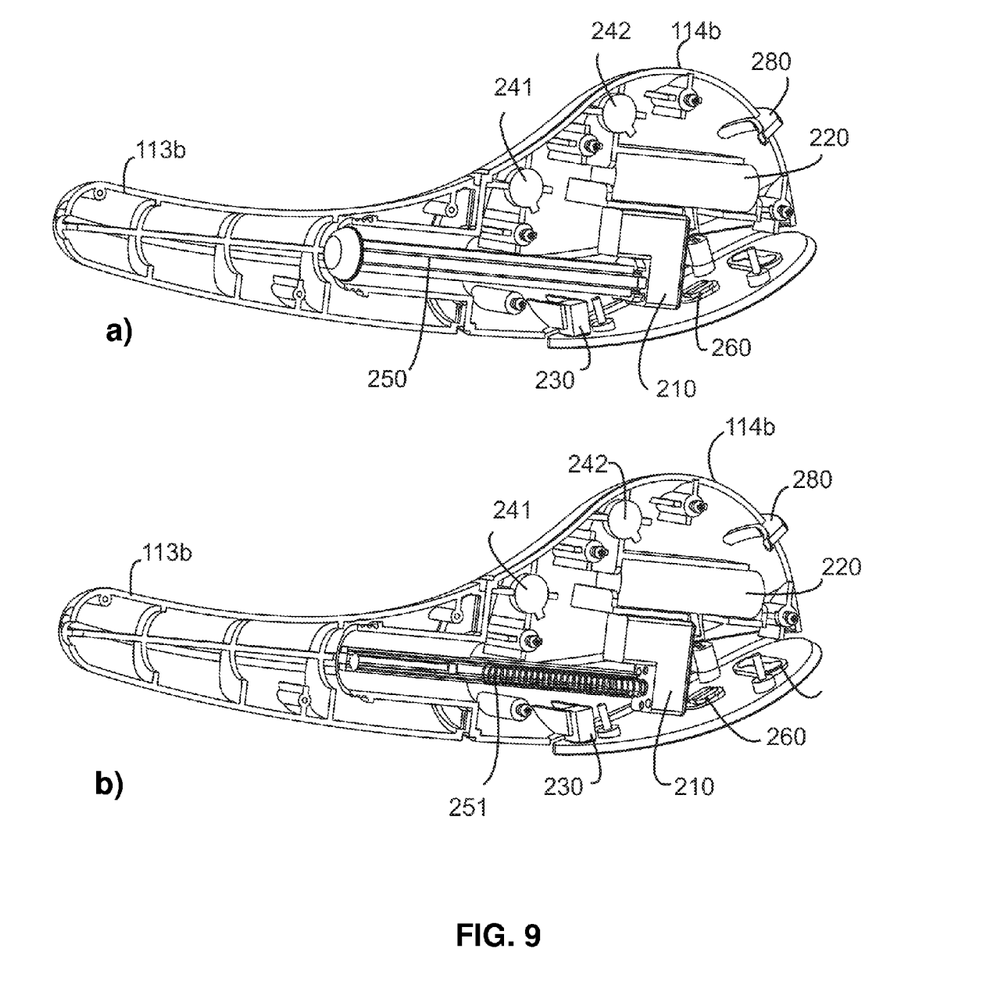
Figure 10:
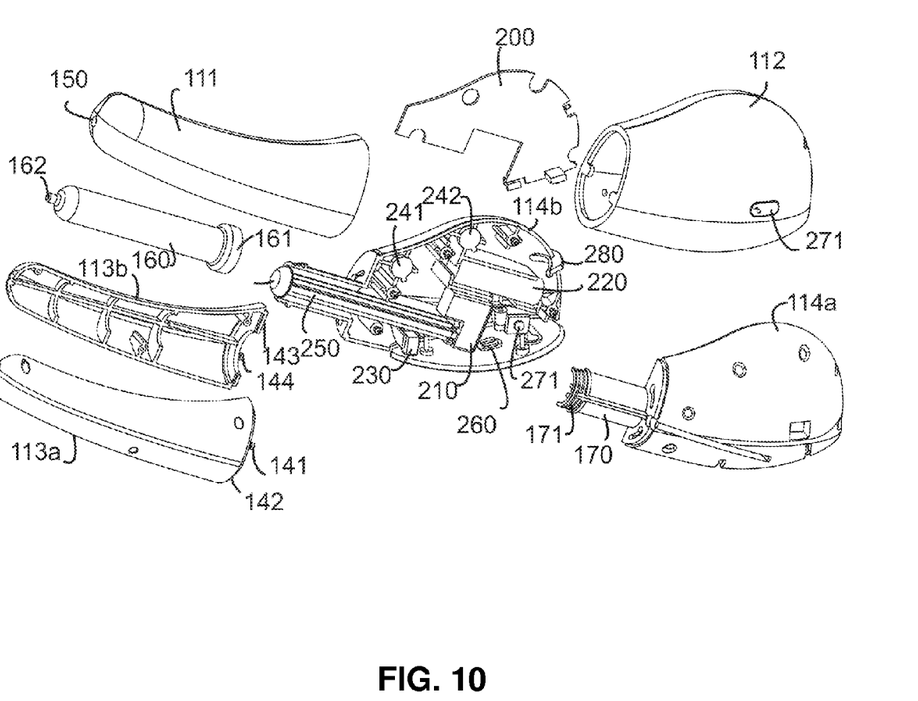
FIG. 10 shows the exploded views of the apparatus with all components.

Referring to FIGS. 8-10, the mechanical and electrical components of the present invention that embedded inside the cylindrical housing and the base housing are shown. The base housing 114 comprises of two symmetrical parts 114 (*a-b*) that is embedded a printed circuit board (PCB) 200, an electric motor 210, a battery 220, a charging connector 230, a plurality of small vibrators 241-242, a plunger 250, a slider switch 260, a tact switch 270 and a light pipe 280.

The PCB 200 manages the functionality of the electric motor 210, vibrators 241-242 and the light pipe 280. By pushing a button 271 designed in the exterior portion of the base 120, the electric motor 210 turns on. The electric motor 210 connected to the plunger 250 that has an elongated arm to push the liquid inside the sperm container 160.

A user with his/her partner can be ensured that sperms will be properly delivered onto the cervix. In addition, by sexually stimulating the user before delivering the sperm, the sperm uptake into the uterus increases, thus increasing the probability of fertilization. When the sperm is placed inside the sperm container 160, the user may turn on the apparatus 100 by the slider switch located at the bottom of the base 120. By turning on the apparatus 100, the light pipe 280 shows that the battery life is sufficient for the delivery of sperm to the cervix and it is ready for the operation. The present invention can eject the sperm at a specific velocity and specific time (female orgasm) so that it ensures the best result for delivering the sperm to the cervix and causing fertilization.

The processor designed in the PCB 200 manages all functionality of the mechanical and electrical components. The PCB 200 can manage to deliver the sperm at a specific velocity so that it ensures the best delivery to the cervix. The PCB 200 also can manage to cause pleasurable feelings during the operation. With the addition of pleasurable feelings to the user, the present invention can aid in the induction of a female orgasm and thereby potentially increase the likelihood of fertilization.

The processor can be configured to eject sperm in a constant jet stream type of fashion or to eject in several pulses in order to simulate a physiological ejaculation. The processor in PCB 200 can manage to deliver the sperm in a constant jet stream. The constant jet stream of the sperm can deliver to cervix by pushing the whole length of the plunger. In this case, the whole length of the plunger is moved through the sperm container to introduce semen to the cervix.

The processor in PCB 200 can manage to deliver the sperm in several pulses in order to simulate a physiological ejaculation. Several pulses to simulate a physiological ejaculation can be obtained by pushing the plunger inside the sperm container partially.

During ICI sperm must be delivered onto the cervix with a precise velocity or force that allows the sperm to reach the surface of the cervix during expulsion, however, the force should not be such that it results in sperm being reflected of the walls of the cervix. The PCB 200 can manage the proper force for the sperm when they reach to the surface of the cervix to prevent reflection.

Too small of a volume of sperm delivered can cause back flow out of the cervical canal which may result in insufficient insemination. In order to increase the success of fertility it is most important to regulate the flow of sperm toward the cervical canal. The PCB 200 can regulate the flow of sperm toward the cervical canal to prevent back flow out of the cervical canal.

The cylindrical body 110 may be a simple cylindrical shape, a penis-like shape or another shape that can be used to provide pleasure. The size of the cylindrical body 110 can vary based on user preference.

The cylindrical body 110 has an opening 150 at its distal end 101 which is the where sperm or any type of liquid is ejected. As shown in FIGS. 1-10, the cylindrical body 110 will contain a cylindrical housing 113 of a predefined diameter that is made of flexible plastic or another material. The sperm container 160 contains a unit of semen, or washed sperm, or any type of liquid that the user has decided to use.

For achieving the best results with ICI it is important that the sperm be delivered close or onto the cervical opening, therefore the force and velocity of the ejected sperm should be regulated as to maximize the amount of sperm that is deposited in the desired area.

The female orgasm has been shown to result in increased ability of the uterus to uptake sperm deposited in the vagina, thus increasing the probability of fertility. The button 271 can be set to eject the sperm at a pre-arranged time or may be activated by user preference. The button 271 can be configured to eject sperm in a constant jet stream type of fashion or to eject in several pulses in order to simulate a physiological ejaculation. This can be done by having the electric motor 210 to stop power in a periodic time.

As shown in FIG. 9, the plunger 250 is moved along the sperm container 160 by a force provided by a screw 251. The electric motor revolves the screw 251 around itself and push the plunger 250 inside the sperm container 160.

FIG. 10 shows an exploded view of the present invention with all electrical and mechanical components. For hygienic purposes, the sperm container and the plunger can be disposable and user can change it for each usage.

Alternative embodiments can be made to increase pleasure of the user. In addition to the shape of the present device that is designed to induce pleasure, the present invention also contains a plurality of vibrators 241-242. The vibration function is achieved by vibrating motor that is inserted in the specific location to stimulate the vagina. The battery 220 will be used to provide power for the vibrating motors 241-242 and the electric motor 210.

Figure 11:
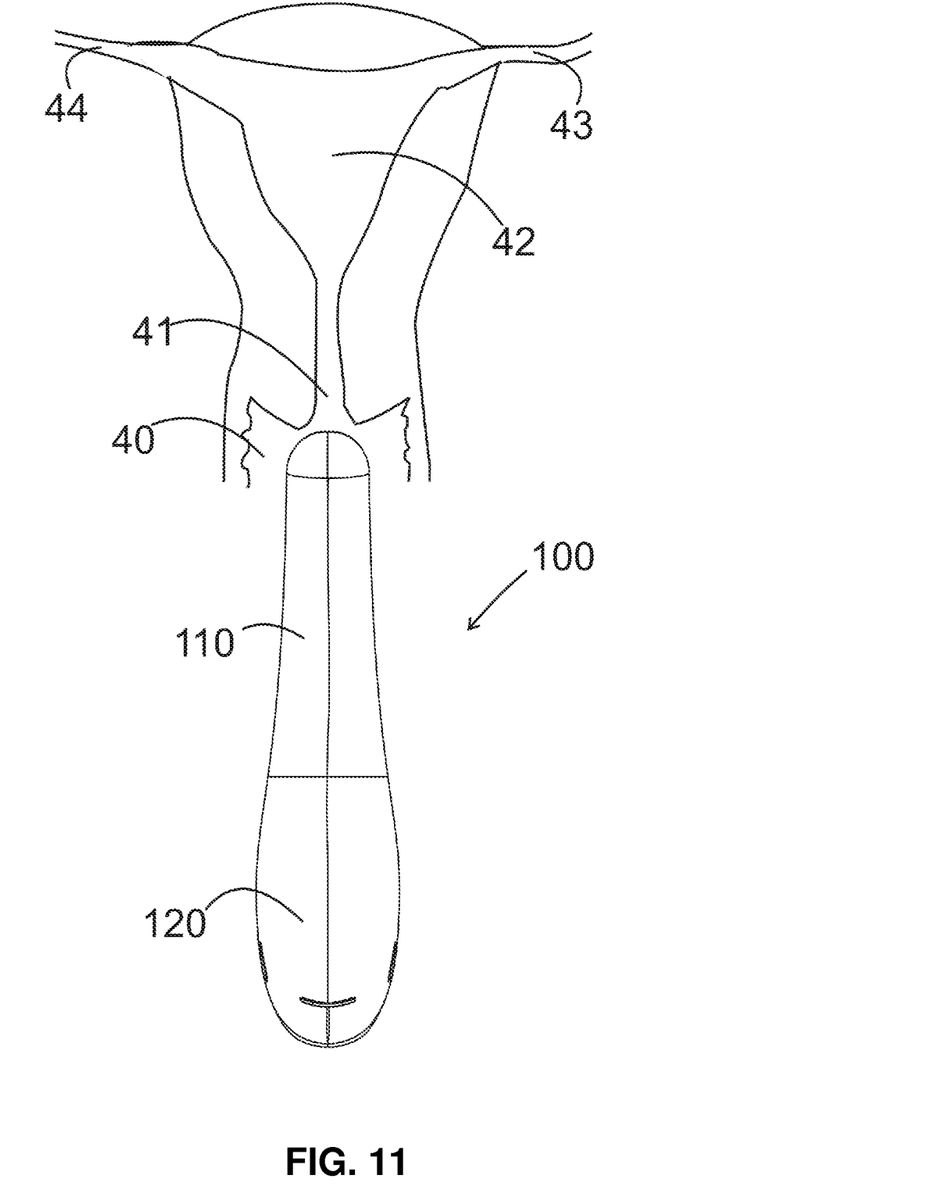
FIG. 11 shows a method for ICI using the present invention.

In all of the embodiments, as shown in FIG. 11, the apparatus 100 is inserted into the vagina 40 and can be operated as a conventional dildo. If the apparatus 100 contains a vibrating motor that function may be turned on in order to increase the pleasurable feelings. At the desired or prearranged time, the sperm can be ejected into the vagina 40 with the push of the button 271 on the base 120. The sperm then flows out of the sperm container through the opening 150 in the distal end 101 of the apparatus 100. The use of the steady stream form the syringe pump mechanism aims to ensure that the majority of the sperm arrive at or near the cervix 41. The sperm can then travel through the cervical canal 41 the uterus 42 and fallopian tubes 43-44 and attempt to fertilize an egg if there is one present.

Figure 12:
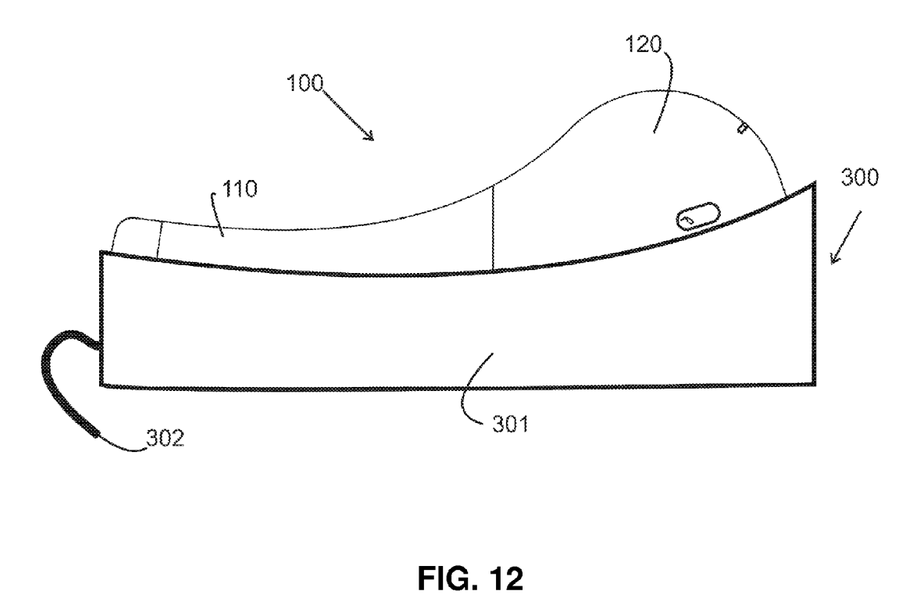
FIG. 12 shows the devices along with a charger port.

Alternatively as shown in FIG. 12, the apparatus 100 may contain a charger 300 with a charging slot in a charging base 301 with a power cord 302 that can be plugged into an electrical outlet that will provide power for recharging the battery.

The vibration function of the present invention works by having a plurality of vibrators 241-242 attached at certain points of the apparatus. In one embodiment of the present invention, the device could contain vibrating motors at the proximal and distal ends of the apparatus. The vibration can be turned off during the time that the sperm is ready to be ejected from the opening 150. An optional attachment that can provide additional stimulation to the clitoris can be attached. In this manner, the device can provide pleasure and thereby attempt to induce a female orgasm after the sperm have been ejected out of the device through the opening 150. The induction of an orgasm may aid in the success of the fertility treatment.

In another embodiment of the present invention, the apparatus has a touch screen interface to communicate with a user and show the different operation options of the apparatus. The options comprises of battery level, flow rate, total remaining time to deliver the liquid, liquid volume indicator, and selecting from variety modes for delivery.

In order to further simulate physiological sexual intercourse, the device may contain a harness mount that can be attached to or is a part of the apparatus. The harness mount can be inserted in a standard sized hole in most harnesses. The apparatus can then function in the same manner as previously described. Additionally, the shape of the apparatus may be straight and cylindrical, it may curve near the proximal or distal ends or in the middle and may curve multiple times. The length of the apparatus at either end of such a curve can vary. The apparatus can also be made to vaginally enter at both proximal and distal ends with the ejecting means.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

With respect to the above description, it is to be realized that the optimum relationships for the parts of the invention in regard to size, shape, form, materials, function and manner of operation, assembly and use are deemed readily apparent and obvious to those skilled in the art, and all equivalent relationships to those illustrated in the drawings and described in the specification are intended to be encompassed by the present invention.

What is claimed is:

1. An apparatus for artificial insemination comprising of:
   k. a housing comprising of:
      i. a body,
      ii. a cylindrical tube projected outwardly from said body,
      iii. a syringe barrel having a first end and a second end, the first end engaging with said cylindrical tube, and the second end having an aperture, whereby a fluid is stored in said syringe barrel,
      iv. a plunger fitted inside said cylindrical tube, and
      v. means to extend said plunger from said cylindrical tube through said syringe barrel,
   l. an inserting part having a distal end and a proximal end, said inserting part having an inner cavity sized to receive said syringe barrel from the proximal end and an opening at said distal end to be aligned with said aperture, said inserting part is inserted into a vagina from said distal end,
   m. means to attach said housing to said inserting part, whereby moving said plunger along said syringe barrel expels said fluid through said opening.

2. The apparatus for artificial insemination of claim 1, wherein means to extend said plunger comprising:
   a. an electric motor having a threaded shaft to provide rotational movement;
   b. said shaft is in threaded engagement with said plunger;
   d. a battery to provide power to said electric motor;
   f. a processor to control said electric motor; and
   g. a switch to activate said electric motor.

3. The apparatus for artificial insemination of claim 1, wherein said fluid being selected from the groups consisting of a unit of semen and a washed sperm.

4. The apparatus for artificial insemination of claim 2, wherein said electric motor being a stepper motor with variable speed settings.

5. The apparatus for artificial insemination of claim 1, further having a plurality of vibrators to provide vibrational movement for stimulating.

6. The apparatus for artificial insemination of claim 2, wherein said power supply being a battery or an electrical outlet.

7. A method to eject sperm cells by a steady stream or in a separate spray to ensure that the majority of the sperm arrive at or near the cervix, comprising of:
   f. obtaining an apparatus for artificial insemination, wherein said apparatus comprising of
      a. a housing comprising of:
         i. a body,
         ii. a cylindrical tube projected outwardly from said body,
         iii. a syringe barrel having a first end and a second end, the first end engaging with said cylindrical tube, and the second end having an aperture, whereby a fluid is stored in said syringe barrel,
         iv. a plunger fitted inside said cylindrical tube,
         v. means to extend said plunger from said cylindrical tube through said syringe barrel,
      b. an inserting part having a distal end and a proximal end, said inserting part having an inner cavity sized to receive said syringe barrel from the proximal end and an opening at said distal end to be aligned with said aperture, said inserting part is inserted into a vagina from said distal end,
      c. means to attach said housing to said inserting part,
   g. filling said syringe barrel with sperm cells;
   h. attaching said syringe barrel to said cylindrical tube;
   i. bringing said apparatus in position with the user's cervix;
   j. sexually stimulating the user with said apparatus, and
   k. pushing an ejection button on said apparatus to expel sperm cells into the user's cervix when the user is stimulated,
      whereby increasing the probability of successful insemination.

8. The apparatus for artificial insemination of claim 1, wherein said cylindrical tube further having a threaded end to be engaged with said syringe barrel.

9. The apparatus for artificial insemination of claim 1, wherein said means to attach said housing to said inserting part comprising of a plurality of apertures in said housing sized to receive a plurality of pins designed in said proximal end of said inserting part.

10. The apparatus for artificial insemination of claim 1, wherein said inner cavity having means to tightly hold said syringe barrel inside said inserting part.

* * * * *